(12) United States Patent
van den Bosch et al.

(10) Patent No.: US 10,405,507 B2
(45) Date of Patent: Sep. 10, 2019

(54) BROCCOLI TYPE ADAPTED FOR EASE OF HARVEST

(71) Applicant: Seminis Vegetable Seeds, Inc., St. Louis, MO (US)

(72) Inventors: Franciscus van den Bosch, Kesteren (NL); Meinardus P. Boon, Hoorne (NL)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

(21) Appl. No.: 15/833,864

(22) Filed: Dec. 6, 2017

(65) Prior Publication Data

US 2018/0153118 A1 Jun. 7, 2018

Related U.S. Application Data

(63) Continuation of application No. 15/145,907, filed on May 4, 2016, now Pat. No. 9,861,045, which is a continuation of application No. 13/272,117, filed on Oct. 12, 2011, now Pat. No. 9,332,699, which is a continuation of application No. 12/656,445, filed on Jan. 29, 2010, now abandoned, which is a continuation of application No. 10/850,077, filed on May 19, 2004, now Pat. No. 8,030,549.

(51) Int. Cl.
*A01H 5/02* (2018.01)
*A01H 5/00* (2018.01)

(52) U.S. Cl.
CPC .................. *A01H 5/02* (2013.01); *A01H 5/00* (2013.01)

(58) Field of Classification Search
CPC ............. A01H 6/20; A01H 6/203; A01H 1/02
USPC ................................................. 800/260, 306
See application file for complete search history.

(56) References Cited

PUBLICATIONS

Antonious et al., "Impact of Soil Amendments on Broccoli Quality and Napropamide Movement Under Field Conditions," *Bulletin of Environmental Contamination and Toxicology*, 75(4):797-804 (2005), in prior U.S. Appl. No. 12/656,445.
Baggett et al., "Broccoli Breeding Lines OSU 101-OSU 105," *HortScience* 20(4):782-784 (1985), in prior U.S. Appl. No. 12/656,445.
Baggett, "Broccoli Breeding," Report to the Oregon Processed Vegetable Commission, 1986, 5 pages (1986), in prior U.S. Appl. No. 13/272,117.
Baggett, "Broccoli Breeding," Report to the Oregon Processed Vegetable Commission, 1987, 5 pages (1987), in prior U.S. Appl. No. 13/272,117.
Baggett, "Broccoli Breeding," Report to the Oregon Processed Vegetable Commission, 1988, 8 pages (1988), in prior U.S. Appl. No. 13/272,117.
Baggett, "Broccoli Breeding," Report to the Oregon Processed Vegetable Commission, 1989, pp. 38-31 (1989), in prior U.S. Appl. No. 13/272,117.
Baggett, "Broccoli Breeding," Report to the Oregon Processed Vegetable Commission,1991-1992, pp. 30-30 (1992), in prior U.S. Appl. No. 13/272,117.
Baggett, "Broccoli Breeding," Report to the Oregon Processed Vegetable Commission, 1992-1993, pp. 23-28 (1993), in prior U.S. Appl. No. 13/272,117.
Baggett, "Broccoli Breeding," Report to the Oregon Processed Vegetable Commission, 1993-1994, 8 pages (1994), in prior U.S. Appl. No. 13/272,117.
Baggett, "Broccoli Breeding," Report to the Oregon Processed Vegetable Commission 1994-1995, pp. 41-47 (1995), in prior U.S. Appl. No. 13/272,117.
Baggett et al., "Inheritance of Intermode Length and its Relation to Head Exertion and Head Size in Broccoli," *J. American Society Hort. Science* 120(2):292-296 (1995), in prior U.S. Appl. No. 12/656,445.
Baggett, "Broccoli Breeding," Report to the Oregon Processed Vegetable Commission, 1995-1996, pp. 40-45 (1996), in prior U.S. Appl. No. 13/272,117.
Baggett, "Broccoli Breeding," Report to the Oregon Processed Vegetable Commission, 1996-1997, pp. 88-92 (1997), in prior U.S. Appl. No. 13/272,117.
Bon, "Senior Design Project Development of a Non-Selective Broccoli Harvester," *American Society of Agricultural Engineers* (St. Josphe, Michigan), No. 97-1018, presentation at the 1997 International American Society of Agricultural Engineers Meeting, Minneapolis Convention Center, Minneapolis, Minnesota, Aug. 10-14, 1997; pp. 1-17 (1997), in prior U.S. Appl. No. 12/656,445.
Casada et al., "Single Pass Harvesting of Broccoli," *American Society of Agricultural Engineers* (St. Joseph, Michigan), presentation at the 1988 International Summer Meeting of the ASAE, Rushmore Plaza Civic Center, Rapid City, South Dakota, Jun. 16-29, 1988; 11 pages (1988), in prior U.S. Appl. No. 12/656,445.
Dellacecca, "New Agrotechniques to Promote Broccoli Picking," *Proc. Int. Sym. on Brassicas*, Ninth Crucifer Genetics Workshop, Ed. J.S. Dias, I. Crute, A.A. Monteiro Acta Hort. (ISHS) 407:347-352 (1996), in prior U.S. Appl. No. 12/656,445.
International Search Report, International Application No. PCT/US05/17974 (published as WO 05/112610), 2 pages (Feb. 28, 2008), in prior U.S. Appl. No. 13/272,117.
Lenker, "Factors Limiting the Harvest Mechanization of Some Major Vegetable Crops in the U.S.A.," *Fruit, Nut, Vegetable Harvesting Mechanization Symposium*, U.S. Department of Agriculture, Agricultural Research Service, Salinas California; pp. 29-38 (1984), in prior U.S. Appl. No. 12/656,445.

(Continued)

*Primary Examiner* — Keith O. Robinson
(74) *Attorney, Agent, or Firm* — Alissa M. Eagle; Arnold & Porter Kaye Scholer LLP (57) ABSTRACT

A broccoli plant characterized in having an exerted head having a crown higher than the leaf canopy and a harvestable head of at least about 200 grams when planted at a density of 40,000 plants per hectare, where the harvestable head comprises the top 25 centimeters of said stalk.

20 Claims, 8 Drawing Sheets
(7 of 8 Drawing Sheet(s) Filed in Color)

(56) References Cited

PUBLICATIONS

McLaurin et al., "Broccoli—Commercial vegetative production," The University of Georgia Cooperative Extension, Circulare 764 (2010), in prior U.S. Appl. No. 10/850,077.

Myers, "Broccoli Breeding and Evaluation," Report to the Oregon Processed Vegetable Commission, 1997-1998, pp. 126-134 (1998), in prior U.S. Appl. No. 13/272,117.

Myers, "Broccoli Breeding and Evaluation," Report to the Oregon Processed Vegetable Commission, 1998-1999, pp. 108-128 (1999), in prior U.S. Appl. No. 13/272,117.

Myers, "Broccoli Breeding and Evaluation," Report to the Oregon Processed Vegetable Commission, 1999-2000, pp. 110-123 (2000), in prior U.S. Appl. No. 13/272,117.

Myers, "Broccoli Breeding and Evaluation," Report to the Oregon Processed Vegetable Commission, 2000-2001, pp. 150-161 (2001), in prior U.S. Appl. No. 13/272,117.

Myers, "Broccoli Breeding and Evaluation," Report to the Oregon Processed Vegetable Commission, 2001-2002, pp. 168-180 (2002), in prior U.S. Appl. No. 13/272,117.

Myers, "Broccoli Breeding and Evaluation," Report to the Oregon Processed Vegetable Commission, 2002-2003, pp. 55-64 (2003), in prior U.S. Appl. No. 13/272,117.

Myers, "Broccoli Breeding and Evaluation," Report to the Oregon Processed Vegetable Commission, 2004-2005, pp. 96-104 (2005), in prior U.S. Appl. No. 13/272,117.

Partial European Search Report, European Application No. 05103316 (published as EP 1 597 965), 2 pages (Sep. 15, 2005), in prior U.S. Appl. No. 13/272,117.

Poehlman et al., *"Breeding Field Crops,"* $4^{th}$ ed., Iowa State University Press, Ames, Iowa, p. 473 (1995), in prior U.S. Appl. No. 12/656,445.

Shear et al., "Multiple-Pass Selective Broccoli Harvester Field Trial," presentation at the 1990 International Winter Meeting sponsored by the American Society of Agricultural Engineers (St. Joseph, Michigan), Hyatt Regency Chicago, Chicago, Illinois, Dec. 18-21, 1990; Paper No. 901611; 16 pages (1990), in prior U.S. Appl. No. 12/656,445.

Shearer et al., "A Cut-Off Saw Mechanism for Selective Harvest of Broccoli," *American Society of Agricultural Engineers*, 34(4):1623-1628 (1991), in prior U.S. Appl. No. 12/656,445.

Shearer et al., "Development of a Mechanized Selective Harvester for Cole Crops," American Society of Agricultural Engineers, presentation at the 1991 International Summer Meeting, Albuquerque Convention Center, Albuquerque, New Mexico, Jun. 23-26, 1991; Paper No. 911018; 15 pages (1991), in prior U.S. Appl. No. 12/656,445.

UNILETT Informations, "Chou Brocoli: La Récolte Méchanique Devient Possible," 107:11-13 (2001) (English Translation), in prior U.S. Appl. No. 12/656,445.

BROCCOLI TYPE ADAPTED FOR EASE OF HARVEST

CROSS REFERENCE TO RELATED APPLICATION

This application is a continuation of Ser. No. 15/145,907, filed May 4, 2016 (now U.S. Pat. No. 9,861,045) which is a continuation of U.S. application Ser. No. 13/272,117, filed Oct. 12, 2011 (now U.S. Pat. No. 9,332,699), which is of U.S. application Ser. No. 12/656,445, filed Jan. 29, 2010 (abandoned), which is a continuation of U.S. application Ser. No. 10/850,077, filed May 19, 2004 (now U.S. Pat. No. 8,030,549), which applications are incorporated herein by reference in their entireties.

BACKGROUND OF THE INVENTION

Field of the Invention

The present invention relates to the field of plant breeding and variety development, and more specifically, relates to the development of a new and distinct broccoli type for easier harvest.

Description of Related Art

Broccoli is a native of the Mediterranean region, and has been grown in Italy from at least the time of the Roman Empire. It was a favorite vegetable in Rome where a variety called Calabrese was developed. Before the Calabrese variety was cultivated, Romans ate a purple sprouting broccoli that turned green when cooked.

During the 16th century, the popularity of broccoli spread throughout Europe and it was cultivated in the United States by the late 18th century. However, broccoli did not become a commercially important crop in the United States until after World War II. In the late 20th century broccoli became popular in the United States, and has recently been touted for its health benefits. Presently, the United States is the world's largest producer of broccoli, with most of the broccoli grown in the U.S. marketed as fresh produce. The leading broccoli-producing states are California (with approximately 90 percent of the crop), Arizona, Texas, and Oregon. Broccoli also is grown on a large scale in Spain, northern Europe, Central America and Australia.

Broccoli is a member of the Cruciferae family, as are cabbage, cauliflower, brussels sprouts, kohlrabi, turnips, mustards, and Chinese cabbage. The word broccoli comes from the Italian word "brocco", which means arm branch, more particularly, from the word broccolo, which is the diminutive form of brocco and refers to cabbage sprout. Broccoli is plural and refers to the numerous shoots in this form of *Brassica oleracea*.

There are several types of broccoli, the most popular being the sprouting/Italian broccoli that includes the Calabrese-type, *Brassica oleracea* L convar *bonytis* (L.) Alef. var. *cymosa* Duch. (the name adopted by the Community Plant Variety Office (CPVO)). Heading broccoli has several attributes more commonly attributed to cauliflower (an example being the Romanesco type, which is increasing in popularity). The true Calabrese type is a primitive type with many secondary heads (origination from the axils of the leaves). The heads are also split into smaller parts, that do not form a solid head.

Another broccoli, "broccoli rabe", or, "broccoli raab" has loose green sprouting heads (more like loose broccoli than cauliflower) that are harvested and eaten as greens along with surrounding leaves.

Morphologically, cauliflower and heading broccoli are similar. The broccoli plant, however, generally produces a green head with a longer and more slender floret-stalk than cauliflower. When the main terminal head of a broccoli plant is harvested, the axillary buds lower on the main stem are induced to develop into smaller heads, which can also be harvested.

Much of the breeding of modern varieties has focused on heading types, which have been bred to produce a single, large head at the plant axis, reducing the number of secondary heads, though in some regions after the harvest of the main head secondary heads are still harvested, sometimes referred to as "asparagus broccoli".

The most commonly grown broccoli variety is Marathon, which shows average to good vigor, with the height of the head at about 40-50 cm above the ground, and the height of the canopy at about 60-70 cm. Maturity is medium to late (70 days in the summer from planting), with secondary heads present. The color of the head is grey/green, with the head forming a medium dome in shape. The bead on the heads is fine, the stem diameter is medium, somewhat sensitive to hollow stem, and the variety has intermediate resistance to downey mildew (*Peronospora parasitica*). Marathon is best adapted to cool season cultivation, (fall, winter) and the plant density varieties between 40,000 to 80,000 plants per ha.

Most broccoli varieties grow best on well-drained soils that hold water. In sandy soils, irrigation is important for optimum plant growth and to maintain proper main head and side shoot development. Flower heads (the edible portion of sprouting broccoli) develop relative to ambient temperatures, and in the heat of summer, broccoli heads maturing in July may produce flowers and seeds more quickly (four to six days) than those maturing in the cooler spring and fall periods.

To be considered good quality, broccoli heads should be closed, dark green and tight (no yellow petals showing). A deep green, uniform head color is a desirable trait in broccoli. Broccoli heads "green" according to the amount of sunshine reaching the crown of the heads, the crown being the upper surface of the broccoli head covered by the florets. The present commercial heading broccoli varieties all have a high canopy that shades at least portions of the head, particularly at the margin of the crown, resulting in yellowing around the outer extremities of the harvested broccoli heads, sometimes even causing extensive yellowing of individual florets at the center of the crown.

Broccoli is typically planted in the range of 30,000 to 40,000 plants per hectare, though in North America it is common to plant broccoli at a higher density, of 40,000 to as high 100,000 plants per hectare. At higher densities, the broccoli plants will produce smaller heads. In common with other cole crops, broccoli can be established in the field by direct-seeding or by transplanting. Many factors, such as soil type, organic matter content and soil moisture interact to influence germination and emergence. A more uniform, as well as earlier, broccoli crop can be grown from transplants raised in plugs or flats in a greenhouse. Such transplants can be planted in the field during late April, although the plants must be hardened off before being set out.

The edible portion of broccoli is the unopened flowering heads. Broccoli heads are susceptible to a number of defects that may relate to climatic or growth aberrations, though some appear to be cultivar related. Many defects can be avoided by harvesting at the correct stage so that the heads do not become overmature. A post-mature crop will show advanced flower development, with yellowing of the heads. Over-mature plants also commonly developing fibrous stems.

Harvesting at the correct stage and proper handling afterwards are very important with broccoli, as it is a perishable commodity. For this reason, uniformity of maturity and concentrated harvesting have been the most highly desirable characteristics in broccoli varieties.

Harvested broccoli is often cooled with packed ice or a hydro-cooler immediately after harvest. Broccoli that is cooled and maintained at 32° F. and 95 to 100 percent relative humidity can be stored for 10 to 14 days. If broccoli is stored this long, however, it will begin to lose its dark green color and firmness, affecting its marketability.

Since harvesting is the single most expensive cultural operation, it is imperative that these costs be kept to a minimum. The present trend is to harvest only the main terminal heads, usually by hand. Certain mechanical harvest aids are used, but complete mechanical harvesting has not been adopted. Use of modern, more uniform hybrids has enabled growers to complete harvesting in two or, at the most, three manual cuts through the field.

In a study reviewing harvest practices from 1985-1990 in the United States, the time required for cutting broccoli was reported to be on the order of 60 manhours/ha. Overall costs for cut/pack/haul/cool and sell was reported as $2125/ha, with the cost of the cut alone being $500/ha. The labor requirements for harvesting are well over 50% of the total labor costs for growing broccoli.

Converting from hand to machine harvesting of broccoli could reduce these labor requirements by a great deal. However, in testing different cultivars, transplant times, growing techniques and harvest methods, a recent study determined that once over mechanical harvest of broccoli inflorescences, or heads, compared to the graduated traditional hand-harvest (picking repeatedly 6 to 8 times), results in a yield reduction on the order of 49% to 60%, depending on the variety. A combination of hand harvest for the primary heads, followed by a mechanical picking of the secondary heads was proposed as reducing yield losses, though still on the order of about 23% (Dellacecca, V. 1996, New agrotechniques to promote broccoli picking. Acta Hort. (ISHS) 407:347-352).

There have been efforts aimed at the improvement of broccoli to produce varieties better suited to mechanized harvesting. One factor limiting the performance of a mechanical harvester is the phenotypic appearance of the broccoli varieties and a lack of uniformity in maturity (Casada, J. H.; Walton, L. R.; Bader, M. J. (1988) Single pass harvesting of broccoli, Am Soc Agr Eng Microfiche Collect. (fiche #88-1041) p. 11; Bon, T. A. (1997) Senior design project development of a non-selective broccoli harvester, American Society of Agricultural Engineers No. 97-1018, pp 17). Generally, there is wider acceptable maturity range for processing broccoli compared with fresh market broccoli, which requires a more uniform product (Shearer, S. A.; Jones, P. T.; Casada, J. H.; Swetnam, L. D. (1991). A cut-off saw mechanism for selective harvest of broccoli. Transactions of the American Society of Agricultural Engineers 34 (4): 16231628.)

Thus, the selection of appropriate broccoli plant types for uniformity of maturity has been identified as one factor in the success of any broccoli harvester project (Bon, T. A., 1997). Harvesting of broccoli, either by hand or machine, could also be facilitated by an elongated growth habit that results in the protrusion, or exsertion, of the head above the general level of the broccoli foliage (Baggett, J. R., Kean, D., & Kasimor, K. (1995). Inheritance of internode length and its relation to head exsertion and head size in broccoli, J. Am. Society of Hort Sci. 120 (2): 292-296).

Another issue is that in harvesting broccoli leaves attached to the severed head must be removed manually. Accomplishing this task mechanically presents a further obstacle in the development of full mechanisation of harvest. (Casada Shearer, S. A. and P. T. Jones (1991) Development of a mechanized selective harvester for cole crops, Am Soc of Agr Engineers. Albuquerque, N.M., Jun. 23-26, 1991, Paper #91-1018, p 17). In this regard, incorporating mechanical defoliation of the broccoli plants into a harvester design is an area undergoing investigation, in the hope that successful implementation of a defoliation operation into a harvester would improve the overall efficiency of the harvest and packing (Bon, T. A., 1997). The successful development of mechanized harvest would greatly improve the overall efficiency of the harvest and packing (Bon, T. A., 1997). However, attempts to develop a broccoli harvester have not been successful with present day broccoli plant types, due in part to the many simultaneous problems that must be overcome in adapting broccoli varieties for mechanization. In one article this problem is presented as requiring the selection of varieties with their heads well above the ground, with a more open leaf posture, and with leaves that are well separated from (or uncover) the bottom of the head. (Chou broccoli:La recolte mecanique devient possible. A&D, 07/2001 #68. Also in UNILET informations, #107-Janvier 2001). To date, the development of a broccoli plant type simultaneously providing these multiple solutions in a commercially acceptable context has presented an insurmountable problem for the breeding community.

SUMMARY OF THE INVENTION

The present invention provides a broccoli plant adapted for ease of harvest, with the traits of an exerted head having a crown, or top of the head of the broccoli, that is higher than the leaf canopy and a harvestable head of at least about 200 grams when planted at a density of 40,000 plants per hectare, where the harvestable head comprises the top 25 centimeters of the stalk.

The invention further provides broccoli heads produced by and harvested from such broccoli plants.

In one preferred embodiment, the broccoli plants have a leafless trait along the stalk, such that within 25 centimeters of the crown the plant produces substantially no leaves or petioles having a surface area greater than about 30 square centimeters, more preferably no greater than about 20 square centimeters.

In a further improved embodiment, the broccoli plant produces substantially no leaves or petioles within 25 centimeters of the crown having a surface area of greater than about 10 square centimeters, most preferred being such a plant producing substantially no leaves or petioles within 25 centimeters of the crown.

In another preferred embodiment, the crown of the broccoli plant will be exerted at least about 10 centimeters higher than the topmost leaf of the canopy, more preferably at least about 15 centimeters higher than the topmost leaf of the canopy, and most preferred at least about 25 centimeters higher than the topmost leaf of the canopy.

In one preferred embodiment, the broccoli plant produces a harvestable head of at least about 250 grams, more preferably at least about 350 grams.

In a different preferred embodiment the broccoli plant produces a harvestable head of at least about 120 grams when planted at a density of 80,000 plants per hectare, more preferably at least about 150 grams, and most preferably at least about 200 grams when grown at that density.

The invention also provides a plurality of such broccoli plants grown in a field of broccoli. In a preferred embodiment, substantially all of the plants mature at the same time, and more preferably all of the mature plants grow to substantially the same height.

The present invention also provides a new method of producing a broccoli crop comprising the step of growing a plurality of broccoli plants and harvesting the heads of the broccoli plants by mechanical means, whereby the plants are characterized in having an exerted head having a crown higher than the leaf canopy and a harvestable head of at least about 200 grams when planted at a density of 40,000 plants per hectare, wherein the harvestable head comprises the top 25 centimeters of the stalk, and wherein the mechanical means comprises means for severing the heads and means for collecting severed heads.

In one preferred embodiment, the broccoli plant produces a uniformly green head having substantially no yellowing about the margin of the florets, on the order of about 10% or less of any floret surface showing a change from uniform green to yellow.

In a preferred embodiment of the method of the invention, the mechanical means further comprises means for grasping the heads and guiding the heads to the severing means, more preferably the severing means guided through the plurality of broccoli plants at a substantially constant height above the soil.

In a further preferred embodiment, there is provided means, and collecting means, for advancing the severing means through the plurality of broccoli plants, which are more preferably provided in a combination.

The invention also provides seed of inbred broccoli line designated 932779, a sample of such seed having been deposited as NCIMB 41218 *Brassica oleracea* var botrytis 932779, having a deposit date of 28 Apr. 2004, seed of an inbred broccoli plant designated 970249, a sample of such seed having been deposited NCIMB 41219 *Brassica oleracea* var botrytis 970249, having a deposit date of 28 Apr. 2004, and seed of an inbred broccoli plant designated 970195, a sample of such seed having been deposited as NCIMB 41216 *Brassica oleracea* var botrytis 970195, having a deposit date of 28 Apr. 2004.

The invention further provides hybrid broccoli seed having as one parent a plant grown from such seed, as well as a broccoli plant, or parts thereof, produced by the hybrid seed. The invention thus provides seed of a hybrid broccoli plant designated SVR 4, a sample of such seed having been deposited as NCIMB 41214 *Brassica oleracea* var botrytis SVR 4, having a deposit date of 28 Apr. 2004, seed of an inbred broccoli plant designated SVR 1, a sample of such seed having been deposited NCIMB 41215 *Brassica oleracea* var botrytis SVR 1, having a deposit date of 28 Apr. 2004, and seed of an inbred broccoli plant designated SVR 5, a sample of such seed having been deposited as NCIMB 41217 *Brassica oleracea* var botrytis SVR 5, having a deposit date of 28 Apr. 2004.

In a preferred such embodiment, the invention provides a plurality of such broccoli plants in a field of planted broccoli, as well as broccoli heads harvested from such a field The invention further includes such broccoli plants, or parts thereof, transformed to contain one or more transgenes operably linked to regulatory elements functional in a broccoli plant.

The invention also includes pollen, ovules or tissue culture derived from cells of broccoli seed or plants of the invention, where the tissue culture comprises cells or protoplasts from a tissue from cells from leaves, pollen, embryos, roots, root tips, anthers, flowers, fruit, and seeds, as well as a broccoli plant regenerated from such tissue culture.

The patent or application file contains at least one drawing executed in color. Copies of this patent or patent application publication with color drawing(s) will be provided by the Office upon request and payment of the necessary fee.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various exemplary embodiments of this invention will be described in detail, with reference to the following figures, wherein.

DETAILED DESCRIPTION OF THE PREFERRED EMBODIMENT

Technical or scientific terms used herein shall have the ordinary meaning accepted by those of skill in the art, unless defined differently herein. Descriptions of botanical terms can be found in numerous texts on the subject. See, for instance; Hickey, M., and King, C., (2001). *Cambridge Illustrated Glossary of Botanical Terms*, Cambridge, UK: Cambridge University Press.

Figure 1:
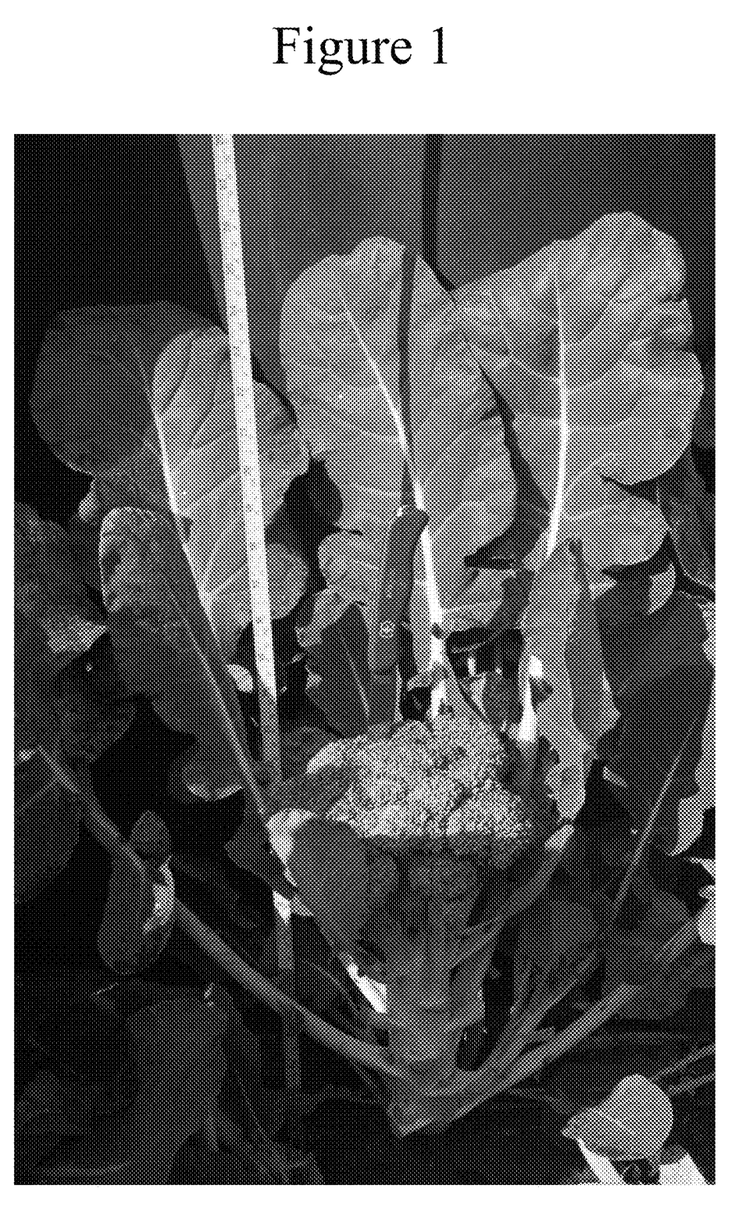
FIG. 1 of the accompanying drawings is a picture showing the typical growth habit of a conventional broccoli line, General, of Seminis Seeds.
Figure 2:
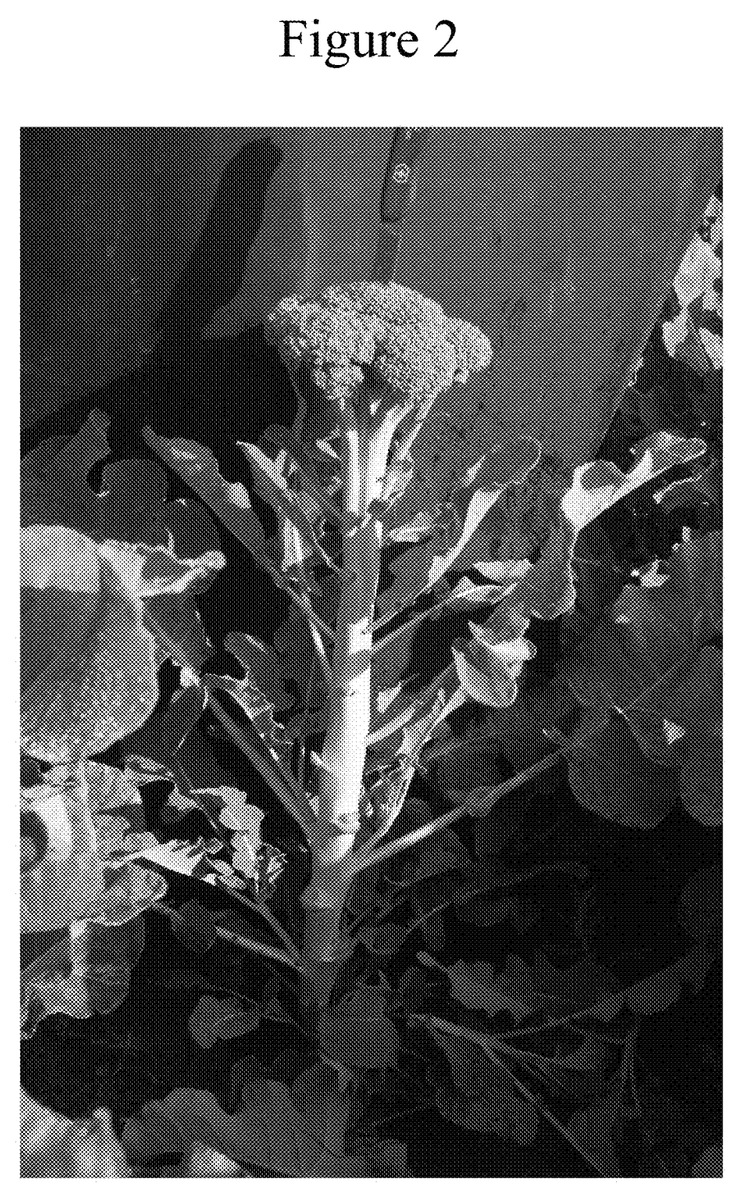
FIG. 2 of the accompanying drawings is a picture showing the growth habit of the hybrid line SVR1.

Referring now to FIG. 1, there is shown a conventional broccoli plant of the line General (Seminis Seeds). FIG. 2 shows a broccoli plant made in accordance with the present invention, the hybrid plant SVR1. The plants in FIG. 1 and FIG. 2 were grown in a field trial under similar conditions. In FIGS. 1 and 2 the leaves facing the camera have been cut away to better reveal the growth habit of the respective plants. The components of a harvested broccoli head comprises the floret clusters, the tops of which form an upper, deep green and generally convex surface, also referred to herein as the crown. Commonly, a region of the stalk supporting the floret clusters is harvested with the broccoli, and forms a part of the edible broccoli head.

The invention provides an inbred line, adapted to 100% mechanical harvest, that combines high head exsertion with a lack of leaf development on the stalk below the head (FIG. 2). Some prior varieties, such as Caravel and Corvet, have shown a relatively raised head but still have large leaves prevalent on the stem directly below the head. There are also purple sprouting varieties with bushy elevated heads, again, that have many leaves on the stem below the head.

The type of broccoli described herein makes it possible to mechanically harvest a field of broccoli, with the trait of a broccoli plant having head exsertion above the plant canopy combined with a substantial absence of leaves and leaflets along the stalk immediately below the head. The variety also produces broccoli plants showing uniformity for both maturity and height, and that will produce commercially acceptable heads.

With the present invention a harvester especially adapted for harvesting the high head exsertion types is also provided, with cutting means provided for severing the heads at a point along the stalks and above the canopy, and means for collecting and conveying the severed heads.

Conventional broccoli typically has large leaves and petioles growing out of the stem up to and just below the head. The improved variety has only a few very small leaves at the same positions below the head.

The development of commercial broccoli hybrids involves the development of homozygous inbred parental lines through techniques well known to the art. Generally, two or more germplasm sources or gene pools are combined to develop superior breeding lines. Desirable inbred or parent lines are developed by continuous selection, followed up with several generations of selfing until the lines are sufficiently uniform. Alternatively, anther or microspore culture (DH lines) may be used followed by selection of the best breeding lines and testing progeny in various hybrid combinations.

Once the inbred lines that give the best hybrid performance have been identified, hybrid seed can be produced indefinitely, as long as the homogeneity and the homozygosity of the inbred parents is maintained. The term inbred broccoli plant also includes any single gene conversions of that inbred. The term single gene converted plant as used herein refers to those broccoli plants which are developed by a plant breeding technique called backcrossing wherein essentially all of the desired morphological and physiological characteristics of an inbred are recovered in addition to the single gene transferred from the donor parent into the inbred via the backcrossing technique.

Figure 3:
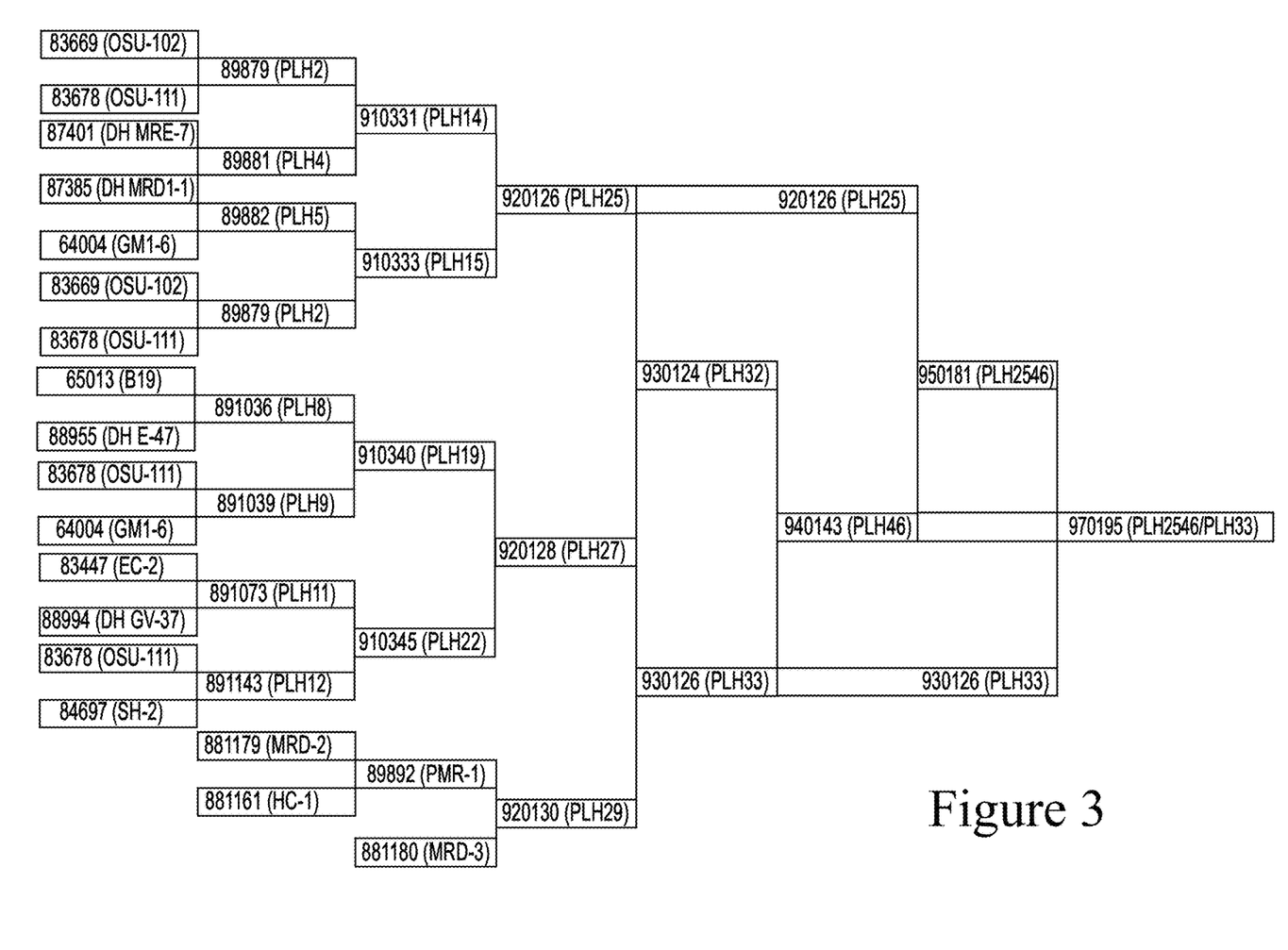
FIG. 3 of the accompanying drawings is a pedigree showing the development of the broccoli plant of the invention designated 970195.

For large scale hybrid seed production, different systems of cross pollination, based on self-incompatibility, or, alternatively, cytoplasmic male sterility (CMS), are used. These techniques are well known in the art. Large scale increase of the hybrid parents (inbred lines) is done by self-pollination, where necessary facilitated by increasing the concentration of $CO_2$ to overcome the self-incompatibility, or bud pollination using hand labor. Such large scale increase of inbred lines is most commonly done in a greenhouse or plastic house. This practice of parent line seed production leads to good quality seed and disease control. Inbred plants include broccoli types 970192, 932779, 970249, PLH42 and 970195. FIG. 3 provides a pedigree chart following the selections made in the development of 970195.

The commercial hybrid seed is produced in the open field by inter-planting rows of the seed parent and the pollinator parent, where self-incompatibility or CMS of the seed parent prevents self pollination and ensures the harvesting of hybrid F1 seed, in methods well known in the art.

For broccoli hybrid seed production, the most modern system is using CMS that was introgressed into *Brassica oleracea* from radish. For broccoli hybrid seed production, the modern system uses CMS that was introgressed into *Brassica oleracea* from radish (Ogura, H. (1968). Studies on the new male sterility in Japanese radish, with special reference to the utilization of this sterility towards practical raising of hybrid seed. Mem Fac Agric Kagoshima Univ. 6:39-78).

The head exsertion broccoli parent line has shown uniformity and stability for all traits. The parent lines have been maintained by bud-pollination (in case of self-incompatibility of the hybrid parents of the three homozygous lines deposited), or in case of CMS seed parents pollinated by its maintainer, and planted for a sufficient number of generations, with careful attention to uniformity of plant type, to ensure homozygosity and phenotypic stability. No variant traits have been observed or are expected.

The exerted broccoli type brings the head far above the canopy. The broccoli further has no large leaves in the area of the stalk that is immediately below the head, and so it can be harvested at the level of the stem in a manner that is free of interference of the leaves, including petioles, which not only eases manual harvest but makes possible the efficient once-over mechanical harvesting of the crop, in both cases saving labor costs. Conventional broccoli can only be harvested manually, making it both time consuming and costly as the product sits deep in the crop and the leaves must further be manually stripped from the stem.

The broccoli provides uniformity in other traits that will maximize yield in once-over harvest, including the timing of maturation and growth characteristics of the broccoli on the plant, as well as head exsertion (raised head) trait. The whole head and/or florets of the broccoli inbred line designated 970192 (p1h26/p1h33), shown in FIG. 4, demonstrate these traits.

A further advantage of the new varieties is the uniformity of color, i.e., that the broccoli plants produce heads that stick out of the canopy and are exposed to sunlight to a higher and more consistent degree than for conventional broccoli plants, resulting in a uniformly deep green color for the product, with substantially no yellowing about the margin of the crown. The reduced canopy means that light can better reach all sides of the heads, as well as individual florets, become uniformly green after floretting, instead of being green with yellow edges as is the case with conventional broccoli being shaded along the edges by the leaf canopy. This is a very desirable characteristic for broccoli processors.

By substantially no yellowing, it is meant that the harvested heads, even when viewed from the side, show a uniform deep green color, with very little or no lightening or yellowing a the edges of the crown as a whole. This is also true for individual florets, which have greatly reduced yellowing about the floret margins. It has been observed that for the broccoli heads produced by the plants having the exerted head trait, that less than about 10% of any floret will show a change from a uniform green to yellow at the margins.

The present invention also contemplates a broccoli plant regenerated from a tissue culture of an inbred or hybrid plant of the present invention. Methods are well known in the art for tissue culture regeneration of broccoli, and further that such methods can be used for the in vitro regeneration of broccoli or transformed broccoli (see, e.g., U.S. Pat. No. 5,188,958, Moloney, et al., Feb. 23, 1993).

The development of the head exsertion broccoli type began as an effort to develop broccoli plants for easier hand or mechanical harvest in combination with good horticultural adaptation. For hand or machine harvesting an elongated growth habit of the main stem bearing the broccoli head and protrusion above the leaf canopy was the goal. This character is defined as head exsertion.

Other characteristics thought to be important for ease of harvesting were head height, along with short leaf petioles, facilitating the exsertion of the head above the canopy. Another character selected for was uniformity of head height.

The following examples are intended to illustrate but not to limit the invention.

Example 1

Development of Germplasm

Both proprietary and available public research lines were available having a raised head (RH) trait. For instance, the Oregon State University (OSU) broccoli breeding program had lines with a moderate raised head, and several accessions were obtained from the OSU breeding program. These lines were designated as OSU-102 and OSU-111. These accessions produced poor head size, poor head quality, generally, and leaves on the stem just below the head which rendered such lines unsuitable as parents for commercially viable hybrids. Selection for better raised head traits and higher internode lengths consistently led to lower head weights. (Baggett, et al., 1995). The present invention has found a solution to this problem, as further described herein.

Proprietary accessions selected at the start of the breeding project were designated DH-MRE-7, DH MRD1-1, GM1-6, B19, DH E-47, EC-2, SH2, EC-2, SH-2, DH M-84, HCH, GB-7, HBH-6 and DH GV-37. All of these lines were elite parent lines developed in the Seminis breeding program, that were used for the production of commercial hybrids as long ago as the 1970s. These lines were chosen at least partly to compensate for the defects observed of the horticultural characteristics of the OSU lines.

More specifically, the proprietary lines had very good general combining ability, resistance to disease, particularly to downy mildew (*Peronospora parasitica*), already showed reasonably good RH traits, short leaves about the head, good head height and head-height uniformity, as well as resistance to bacterial soft rot (Erwinia and Pseudomonas bacteria). The main characteristics of each of these lines are summarized in Table 1, below.

TABLE 1

| Accession or line number | Description |
| --- | --- |
| OSU-102 | Compare with OSU111, little more vigor |
| OSU-111 | Small plant, average RH, leaves on stem, large bead |
| DH-MRE-7 | Downey Mildew resistant, good bead |
| DH MRD1-1 | Downey Mildew resistant, good bead |
| GM1-6 | Relatively good raised head, fine bead, good combining ability, used in many commercial Seminis hybrids (Corvet, Cruiser etc), leaves on stem below the head. |
| B19 | Earliness, combining ability, used in commercial Seminis hybrids. |

TABLE 1-continued

| Accession or line number | Description |
| --- | --- |
| DH E-47 | Brings in head weight and color |
| EC-2 | Relatively RH, large bead |
| DH GV-37 | Firmness and bead quality |
| SH-2 | Combining ability, genetic distance, color, vigor, wetrot tolerance |
| HBH-6 | Earliness |
| DH M-84 | Small bead, quality of head, firmness |
| HCH | Compare HBH6 |
| GB-7 | Firmness and bead quality |

The designation DH designates double haploid, and indicates that this line has been developed through either anther culture or microspore culture, followed by chromosome doubling.

In general, the better RH lines had little (OSU) or average (GM1.6, EC2) head quality. In the better quality lines, i.e., having good firmness, bead size, color, Downey Mildew resistance, etc., the RH trait was generally missing. There were no lines available that combined the RH trait with suitable quality, and none that added the trait of substantially no leaves present below the head to give an exserted appearance.

The lines have been continuously crossed and selected in various combinations since the 1980s. Progeny plants (F1) of each cross were selected for their phenotypic appearance for head exsertion in combination with favorable horticultural characteristics for all other important horticultural traits of head traits. The selected plants from the best families were crossed again with other selected plants from other families. Occasionally, between two crossing cycles selected plants were selfed for one or two generations (F2, F3) to obtain better uniformity of the lines.

The best plants of these lines were crossed again. This breeding procedure is known as the modified family selection, as is described in standard text books of plant breeding, i.e., Allard, R. W., Principles of Plant Breeding (1960) New York, N.Y., Wiley, pp 485; Simmonds, N. W., Principles of Crop Improvement (1979), London, UK, Longman, pp 408; Sneep, J. et al., (1979) Tomato Breeding (p. 135-171) in: Breeding of Vegetable Crops, Mark J. Basset, (1986, editor), The Tomato crop: a scientific basis for improvement, by Atherton, J. G. & J. Rudich (editors), Plant Breeding Perspectives (1986); Fehr, Principles of Cultivar Development-Theory and Technique (1987) New York, N.Y., MacMillan.

In the course of the selection program several lines showing favorable characteristics were selected which were designated as PLH, and associated with a sequence number. Surprisingly, there is little or no discernible loss in yield in the raised head type of broccoli. This is somewhat surprising given the amount of additional stalk required to attain exsertion of a heavy head from the foliage.

Only after a succession of years of crossing and selection in combination with one or two generations of selfing was it shown that the genetic linkage that existed between head exsertion and poor horticultural and head quality characteristics could be broken. The progress in any generation was always small and difficult to quantify from generation to generation.

The best lines now available include 970195 (based on selection from the cross PLH 2546 and PLH 33), 970192 (selected from the cross PLH 26 with PLH 33), 970249 (selected from a cross between DH M 84 and MRD 6), 932779 (selected from a cross between PLH 10 and DC3EC6), and PLH 42 (selected from a cross between DC3EC6 and PLH 10). Seed of lines 932779, 970249, and 970195 are the subject of a NCIMB deposit. PLH 10 was itself a selection from a cross of HBH 6 and OSU-111.

A pedigree showing the development of the line 970195 is summarized in FIG. 3, demonstrating a typical series of crosses and selections used in development of the varieties.

Figure 4:
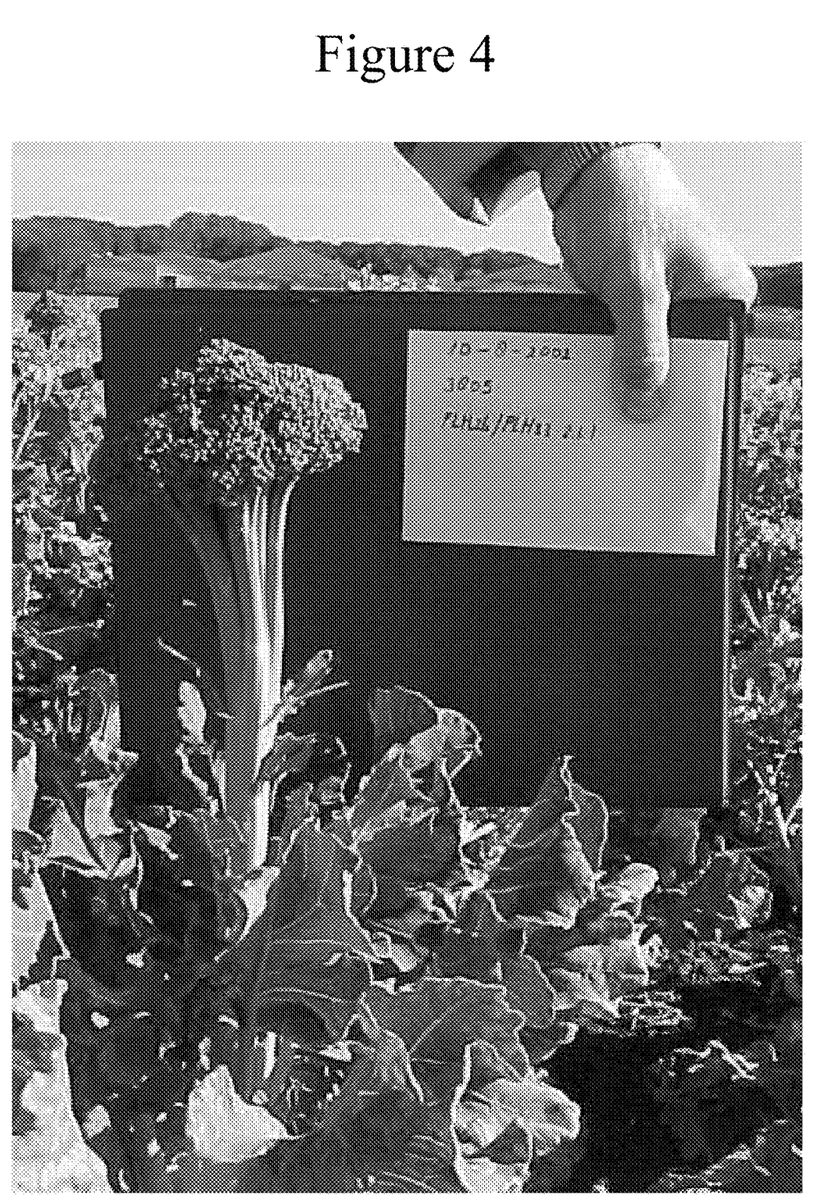
FIG. 4 of the accompanying photographic drawings illustrates a picture of the inbred broccoli plant designated 970192.

The whole head and/or florets of the broccoli inbred line 970192 (p1h26/p1h33), FIG. 4, demonstrates the head exsertion trait in an inbred line. The head exsertion of this broccoli line has shown uniformity and stability for all traits over several years. It has been developed and maintained by bud pollination for five generations with careful attention to uniformity of plant type to ensure homozygosity and phenotypic stability. No variant traits have been observed or are expected.

Inbred lines 970195 and 970249 have similar raised head traits. Development and maintenance of these lines was analogous to that for line 970195.

Figure 5:
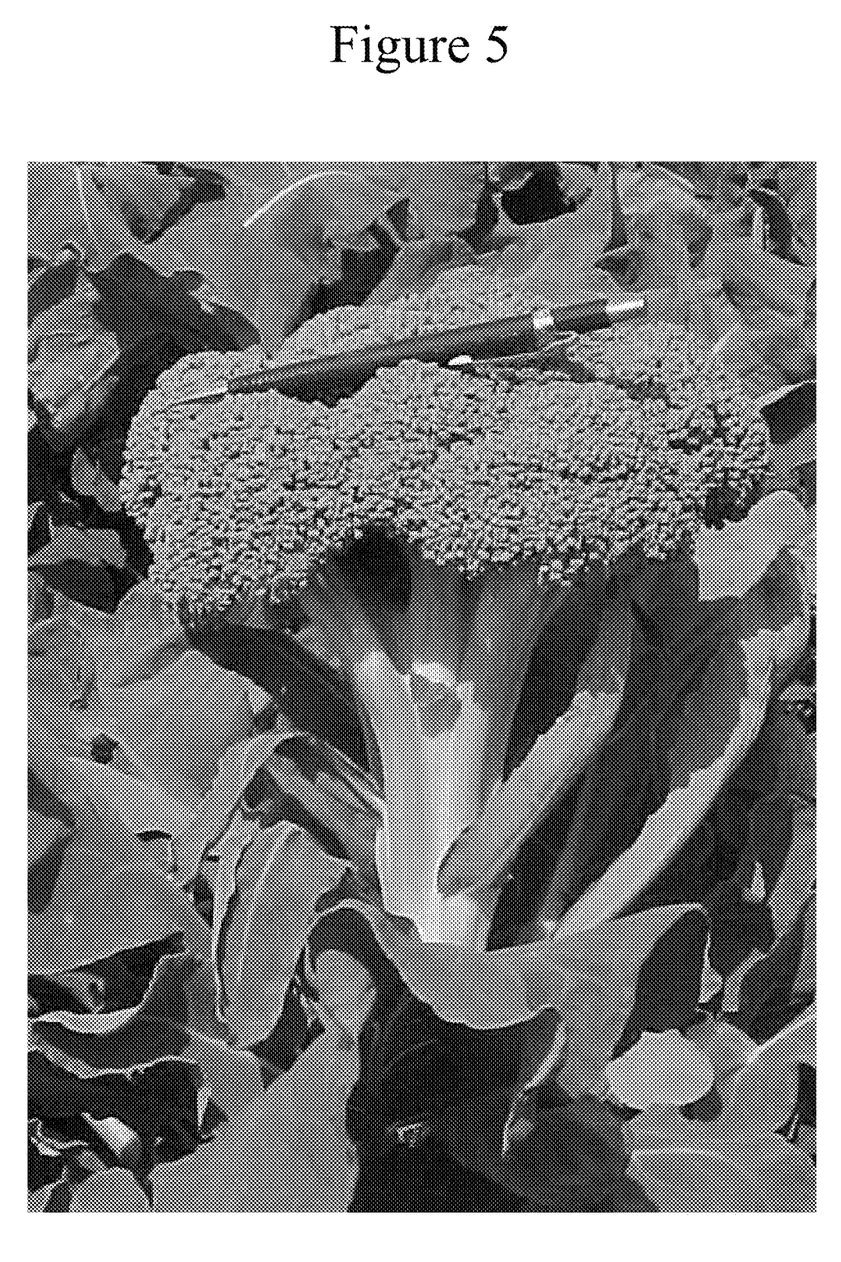
FIG. 5 of the accompanying photographic drawings illustrates a picture of the inbred broccoli plant designated PLH42.

PLH 42 (FIG. 5), shows good head exsertion in accordance with the invention, with few, small leaves present on the stalk below the head. It has been developed and maintained by bud pollination for six generations with careful attention to uniformity of plant type to ensure homozygosity and phenotypic stability. No variant traits have been observed or are expected.

932779 has a similar background to PLH42. It is an early maturing line that shows good head exsertion and a good quality head with nice bead and firmness, with a number of smaller leaves on the stalk below the head. The Downey mildew resistance is very high and the color of the head dark green.

Example 2

Production of Exserted Head Broccoli Hybrid

Figure 6:
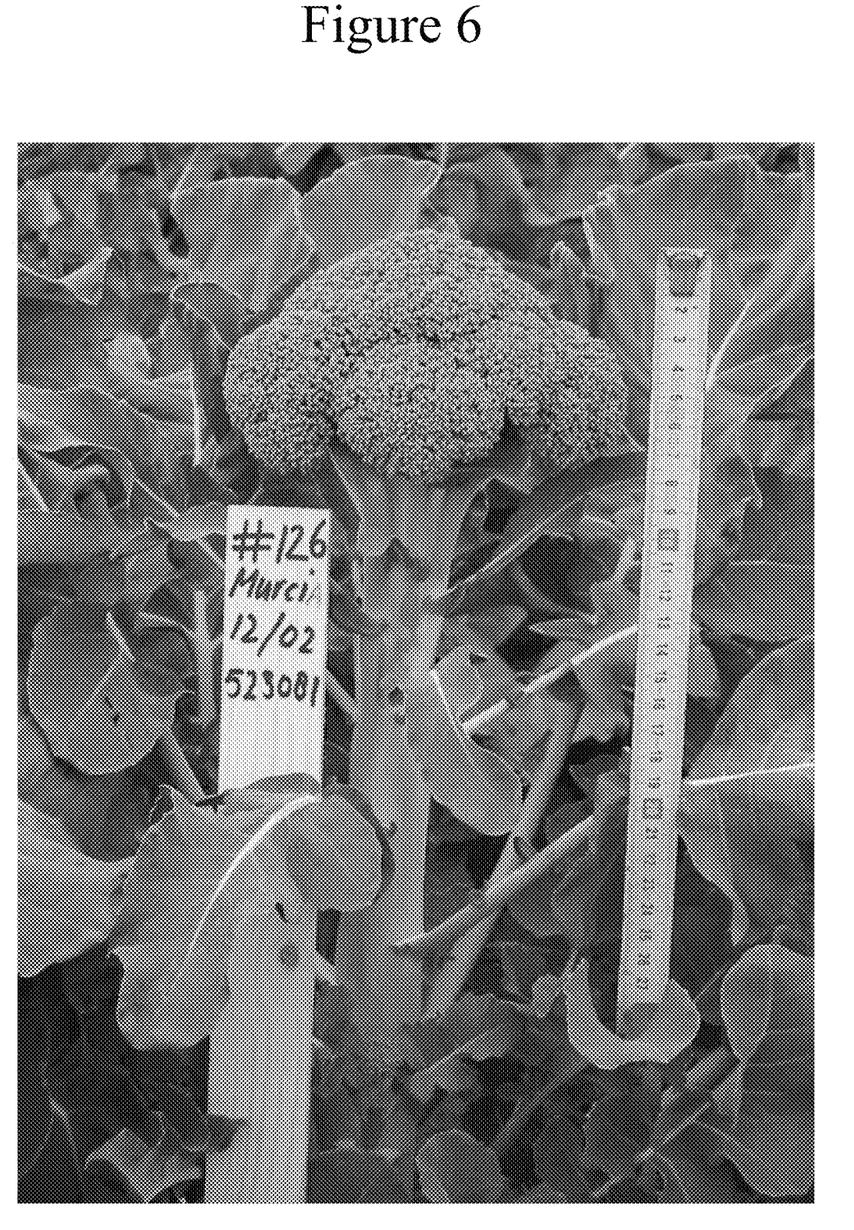
FIG. 6 of the accompanying photographic drawing illustrates a picture of the hybrid broccoli plant designated SVR 1.

The favored inbred lines have been used to produce hybrid combinations. SVR 1 was produced by crossing PLH42×DH PLH13 (FIG. 6). It has the traits of extreme RH, extreme early, extreme dark color, fine bead, good heat tolerance, good wetrot tolerance, good uniformity, Downey Mildew Resistance, DMR, fine stem, some leaves below the head, head weight 250-300 gr/head at 40.000 pl/ha, good adaptability to climate and seasons. The leaves below the head are very few, having a very small square area.

Figure 7:
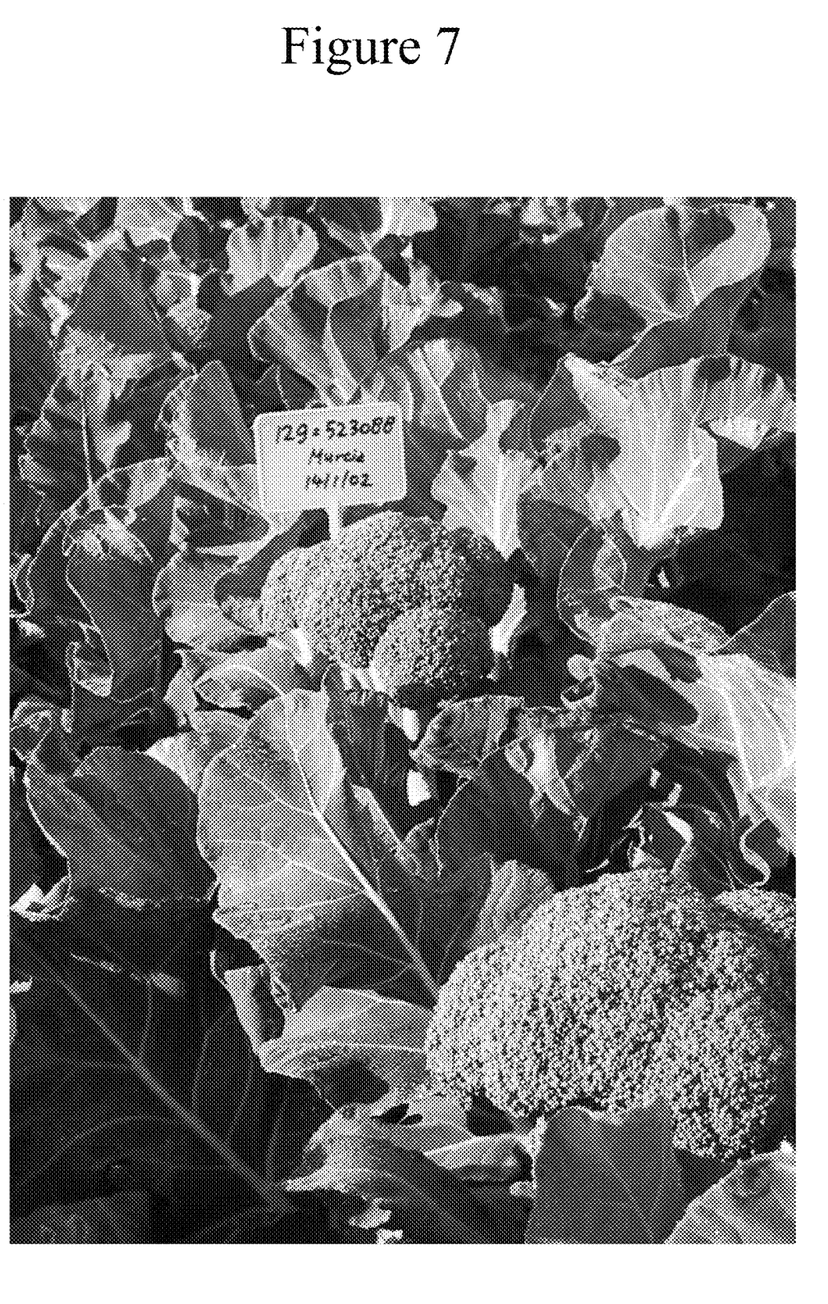
FIG. 7 of the accompanying photographic drawing illustrates a picture of the hybrid broccoli plant designated SVR 4 growing in a field.

SVR 4 was produced by crossing PLH26/PLH33× NjaECB (FIG. 7). It shows good RH, medium maturity, semi crown, relatively large bead, head weight 300350 gr/head at 40.000 pl/ha, with a cleaner stem than SVR1.

Figure 8:
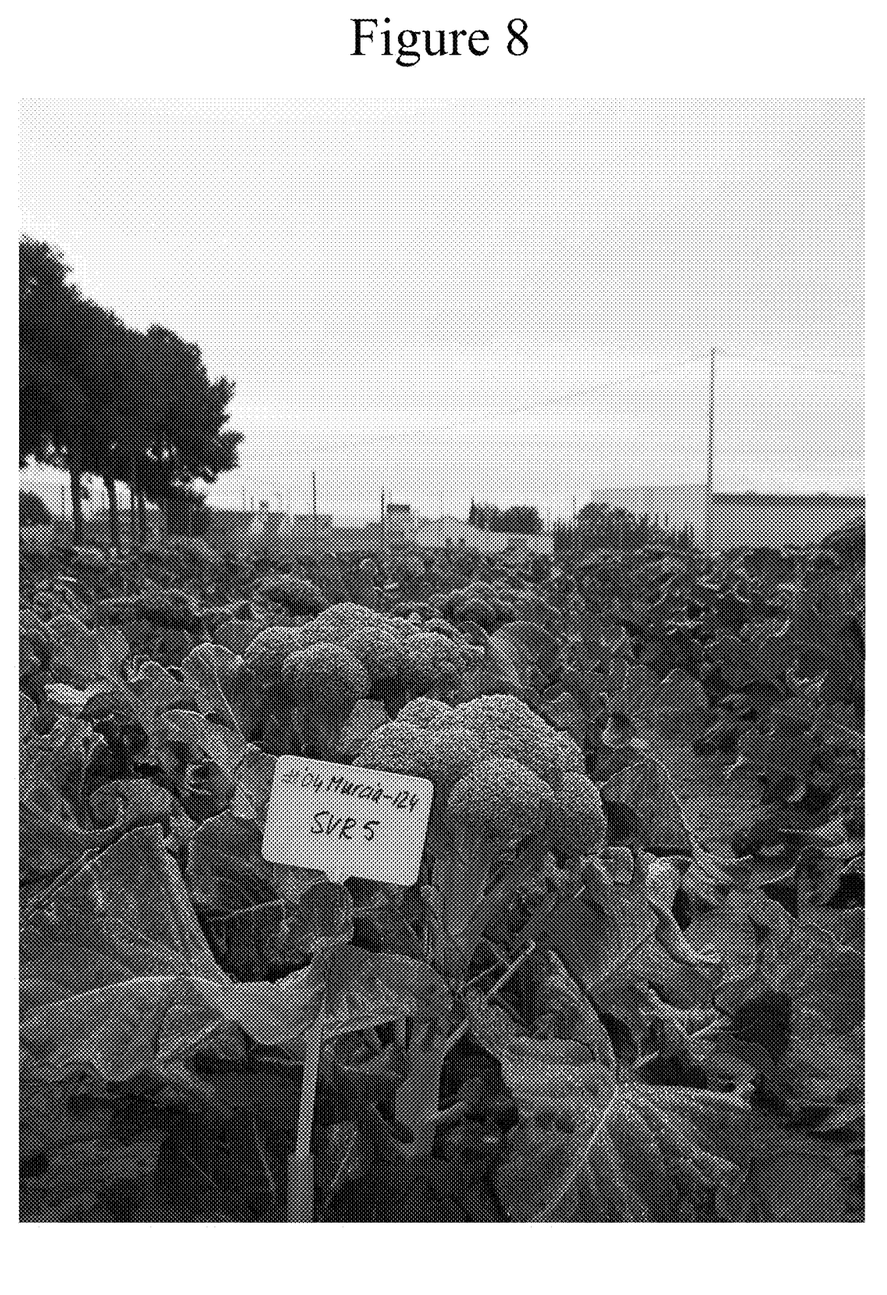
FIG. 8 of the accompanying photographic drawing illustrates a picture of the hybrid broccoli plants designated SVR 5 growing in a field.

SVR 5 was produced by crossing PLH2546/PLH33× NjaECB. Its maturity is like SVR4, deeply branched head, medium raised head, also a cleaner stem than SVR1, head weight 350-400 gr/head at 40,000 pl/ha, extremely green floret color, all green floret, more of a processing/floretting type, with a deeply branched head (FIG. 8).

Example 3

Harvesting of Exserted Head Broccoli

A field of broccoli plants is grown to maturity, and the heads harvested by mechanical means of grasping the heads, severing the heads and collecting the severed heads on a conveyor. It is found that the great majority of broccoli heads can be harvested in this manner from a field of broccoli plants, saving time and expense of hand harvesting. The exserted head trait with little or no foliage below the head allows the running of a mechanized harvest without damage to the broccoli heads or fouling of the harvester.

DEPOSIT INFORMATION

A deposit of the Seminis Vegetable Seeds proprietary inbred and hybrid broccoli lines disclosed above and recited in the appended claims have been made with NCIMB Ltd, 23 St. Machar Drive, Aberdeen AB24 3RY. The date of each of these deposits was 28 Apr. 2004. The deposit of 2500 seeds for each variety were taken from the same deposit maintained by Seminis Vegetable Seeds since prior to the filing date of this application. Upon issuance of a patent, all restrictions upon the deposit will be removed, and the deposit is intended to meet all of the requirements of 37 C.F.R. § 1.801-1.809. The NCIMB accession numbers for inbred lines 932779, 970249, and 970195 are, respectively, NCIMB 41218 *Brassica oleracea* var botrytis 932779, NCIMB 41219 *Brassica oleracea* var botrytis 970249, and NCIMB 41216 *Brassica oleracea* var botrytis 970195. Hybrid broccoli seed SVR 4, SVR 1 and SVR 5 have NCIMB accession number, respectively, NCIMB 41214 *Brassica oleracea* var botrytis SVR 4, NCIMB 41215 *Brassica oleracea* var botrytis SVR 1, and NCIMB 41217 *Brassica oleracea* var botrytis SVR 5. These deposits will be maintained in the depository for a period of 30 years, or 5 years after the last request, or for the effective life of the patent, whichever is longer, and will be replaced as necessary during that period.

The patent or application file contains at least one color drawing executed in color. Copies of this patent or patent application publication with color drawing(s) will be provided by the Office upon request and payment of the necessary fee.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A method of producing hybrid broccoli seed comprising:
   a. planting in a field a first broccoli variety selected from the group consisting of:
      broccoli variety designated 932779, a representative sample of said variety 932779 having been deposited with the NCIMB under NCIMB Accession No. 41218;
      broccoli variety designated 970249, a representative sample of said variety 970249 having been deposited with the NCIMB under NCIMB Accession No. 41219;
      broccoli variety designated 970195, a representative sample of said variety 970195 having been deposited with the NCIMB under NCIMB Accession No. 41216;
      broccoli variety designated SVR 4, a representative sample of said variety SVR 4 having been deposited with the NCIMB under NCIMB Accession No. 41214;
      broccoli variety designated SVR 1, a representative sample of said variety SVR 1 having been deposited with the NCIMB under NCIMB Accession No. 41215; and broccoli variety designated SVR 5, a representative sample of said variety SVR 5 having been deposited with the NCIMB under NCIMB Accession No. 41217;
b. inter-planting a second broccoli variety into said field such that rows in said field alternate between said first and said second broccoli varieties;
c. allowing said first and second broccoli variety to cross pollinate; and
d. harvesting progeny hybrid seed;
wherein one of said first broccoli variety or said second broccoli variety is self-incompatible.

2. A container of hybrid seeds, wherein said hybrid seeds are produced using the method of claim 1.

3. The method of claim 1, wherein a plant grown from said progeny hybrid seed is capable of producing a crown that is exerted at least about 10 centimeters higher than the topmost leaf of the canopy.

4. The method of claim 1, wherein a plant grown from said progeny hybrid seed is capable of producing a crown that is exerted at least about 15 centimeters higher than the topmost leaf of the canopy.

5. The method of claim 1, wherein a plant grown from said progeny hybrid seed is capable of producing a crown that is exerted at least about 25 centimeters higher than the topmost leaf of the canopy.

6. The method of claim 1, wherein a plant grown from said progeny hybrid seed comprises substantially no leaves or petioles having a surface area greater than about 30 square centimeters within 25 centimeters of the crown.

7. The method of claim 1, wherein a plant grown from said progeny hybrid seed comprises substantially no leaves or petioles having a surface area greater than about 20 square centimeters within 25 centimeters of the crown.

8. The method of claim 1, wherein a plant grown from said progeny hybrid seed is capable of producing a uniformly green head having substantially no yellowing about the margin of the florets.

9. The method of claim 8, wherein said uniformly green head has about 10% or less yellow on the floret surface.

10. The method of claim 1, wherein said second broccoli variety is selected from the group consisting of Caravel and Corvet.

11. The method of claim 1, wherein said second broccoli variety is selected from the group consisting of:
broccoli variety designated 932779, a representative sample of said variety 932779 having been deposited with the NCIMB under NCIMB Accession No. 41218;
broccoli variety designated 970249, a representative sample of said variety 970249 having been deposited with the NCIMB under NCIMB Accession No. 41219;
broccoli variety designated 970195, a representative sample of said variety 970195 having been deposited with the NCIMB under NCIMB Accession No. 41216;
broccoli variety designated SVR 4, a representative sample of said variety SVR 4 having been deposited with the NCIMB under NCIMB Accession No. 41214;
broccoli variety designated SVR 1, a representative sample of said variety SVR 1 having been deposited with the NCIMB under NCIMB Accession No. 41215; and
broccoli variety designated SVR 5, a representative sample of said variety SVR 5 having been deposited with the NCIMB under NCIMB Accession No. 41217;
wherein said second broccoli variety is different from said first broccoli variety.

12. A method of producing inbred broccoli seed comprising:
a. planting in a field seed of a first broccoli variety selected from the group consisting of:
broccoli variety designated 932779, a representative sample of said variety 932779 having been deposited with the NCIMB under NCIMB Accession No. 41218;
broccoli variety designated 970249, a representative sample of said variety 970249 having been deposited with the NCIMB under NCIMB Accession No. 41219; and
broccoli variety designated 970195, a representative sample of said variety 970195 having been deposited with the NCIMB under NCIMB Accession No. 41216;
b. allowing broccoli plants grown from said seed to self-pollinate; and
c. harvesting progeny inbred seed.

13. A container of inbred seeds, wherein said inbred seeds are produced using the method of claim 12.

14. The method of claim 12, wherein a plant grown from said progeny inbred seed is capable of producing a crown that is exerted at least about 10 centimeters higher than the topmost leaf of the canopy.

15. The method of claim 12, wherein a plant grown from said progeny inbred seed is capable of producing a crown that is exerted at least about 15 centimeters higher than the topmost leaf of the canopy.

16. The method of claim 12, wherein a plant grown from said progeny inbred seed is capable of producing a crown that is exerted at least about 25 centimeters higher than the topmost leaf of the canopy.

17. The method of claim 12, wherein a plant grown from said progeny inbred seed comprises substantially no leaves or petioles having a surface area greater than about 30 square centimeters within 25 centimeters of the crown.

18. The method of claim 12, wherein a plant grown from said progeny inbred seed comprises substantially no leaves or petioles having a surface area greater than about 20 square centimeters within 25 centimeters of the crown.

19. The method of claim 12, wherein a plant grown from said progeny inbred seed is capable of producing a uniformly green head having substantially no yellowing about the margin of the florets.

20. The method of claim 19, wherein said uniformly green head has about 10% or less yellow on the floret surface.

* * * * *